(12) United States Patent
Qi et al.

(10) Patent No.: US 12,697,238 B2
(45) Date of Patent: Aug. 4, 2026

(54) INTERVENTIONAL INSTRUMENT THAT IS CONVENIENT TO POSITION

(71) Applicant: VENUS MEDTECH (HANGZHOU), INC., Hangzhou (CN)

(72) Inventors: Jesse Jun Qi, Irvine, CA (US); Zhenjun Zi, Hangzhou (CN); Min Frank Zeng, Irvine, CA (US)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 1179 days.

(21) Appl. No.: 17/693,980

(22) Filed: Mar. 14, 2022

(65) Prior Publication Data

US 2022/0257397 A1 Aug. 18, 2022

Related U.S. Application Data

(63) Continuation of application No. PCT/CN2020/116324, filed on Sep. 18, 2020.

(30) Foreign Application Priority Data

Sep. 20, 2019 (CN) .......................... 201910891659.3

(51) Int. Cl.
*A61F 2/24* (2006.01)
*A61F 2/966* (2013.01)

(52) U.S. Cl.
CPC ............ *A61F 2/966* (2013.01); *A61F 2/2436* (2013.01); *A61F 2002/9665* (2013.01); *A61F 2220/0008* (2013.01)

(58) Field of Classification Search
CPC ........ A61F 2/07; A61F 2/2418; A61F 2/2424; A61F 2/2475–2476; A61F 2002/072; A61F 2002/075; A61F 2002/9665
See application file for complete search history.

(56) References Cited

U.S. PATENT DOCUMENTS 5,824,037 A * 10/1998 Fogarty ..................... A61F 2/07
623/1.13
7,226,474 B2 * 6/2007 Iancea ..................... A61F 2/856
623/1.13
(Continued)

FOREIGN PATENT DOCUMENTS

CN 101953723 A 1/2011
CN 104306040 A 1/2015
(Continued)

OTHER PUBLICATIONS

Extended European Search Report Dated Aug. 7, 2023 for corresponding European Application No. 20866830.1.
(Continued)

*Primary Examiner* — Marcia L Watkins

(57) ABSTRACT

Disclosed is an interventional instrument that is convenient to position, comprising a support (1), wherein the support (1) is of a frame structure with a hollowed-out area (11) and is provided with an axis in space, and the support (1) has a loaded state, in which the support is radially compressed, and a released state, in which the support is radially expanded; a sealing film (2), connected to the support (1), and the position of which corresponds to at least part of the hollowed-out area, wherein in the loaded state, the peripheral face of the support (1) is enclosed to form a storage space, and the sealing film (2) is located in the storage space; and a friction increasing component (3) connected to the sealing film (2). According to the interventional instrument, by arranging the friction increasing component (3) and improving the mounting position of the friction increasing component (3), frictional positioning is provided, and adverse effects on loading are also avoided, such that potential safety hazards are eliminated as much as possible.
(Continued)

Further disclosed are a corresponding machining method and an interventional system.

16 Claims, 12 Drawing Sheets

(56) References Cited

U.S. PATENT DOCUMENTS

| | | | | |
|---|---|---|---|---|
| 8,435,283 B2 * | 5/2013 | Jordan | A61F 2/82 | |
| | | | | 623/1.2 |
| 9,517,122 B2 * | 12/2016 | Firstenberg | A61F 2/064 | |
| 10,201,442 B2 | 2/2019 | Lilgegran et al. | | |
| 10,449,049 B2 | 10/2019 | Li et al. | | |
| 10,779,942 B2 | 9/2020 | Rothstein | | |
| 10,874,533 B2 | 12/2020 | Fu et al. | | |
| 2007/0038288 A1 * | 2/2007 | Lye | A61F 2/07 | |
| | | | | 623/1.36 |
| 2009/0125096 A1 * | 5/2009 | Chu | A61F 2/07 | |
| | | | | 623/1.14 |
| 2014/0194805 A1 | 7/2014 | Levine et al. | | |
| 2015/0045880 A1 | 2/2015 | Hacohen | | |
| 2018/0256324 A1 | 9/2018 | Quadri et al. | | |
| 2018/0360632 A1 * | 12/2018 | Kim | A61F 2/966 | |

FOREIGN PATENT DOCUMENTS

| | | |
|---|---|---|
| CN | 209107678 U | 7/2019 |
| WO | WO 2014/144937 A2 | 9/2014 |
| WO | WO 2014/144937 A3 | 9/2014 |
| WO | WO 2017/184385 A1 | 10/2017 |
| WO | WO 2019/006387 A1 | 1/2019 |
| WO | WO 2019/ 006387 A8 | 1/2019 |

OTHER PUBLICATIONS

International Search Report dated Jan. 4, 2021 for corresponding PCT Application No. PCT/CN2020/116234.

* cited by examiner

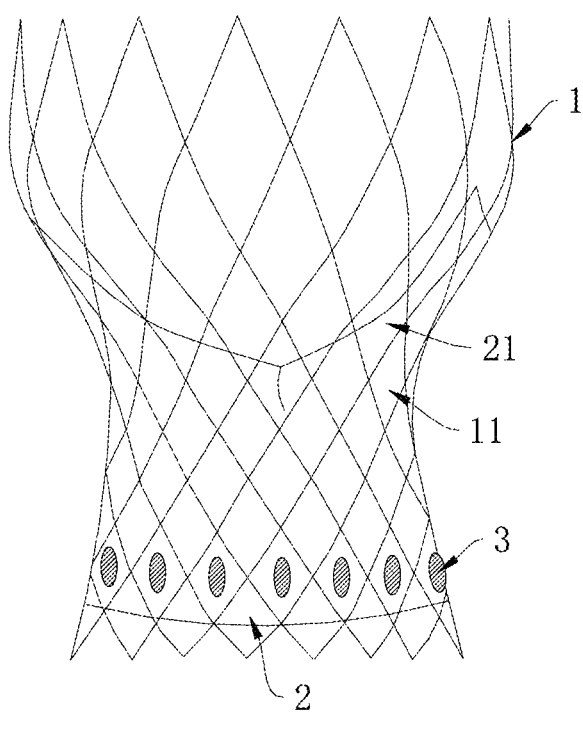
FIG. 1
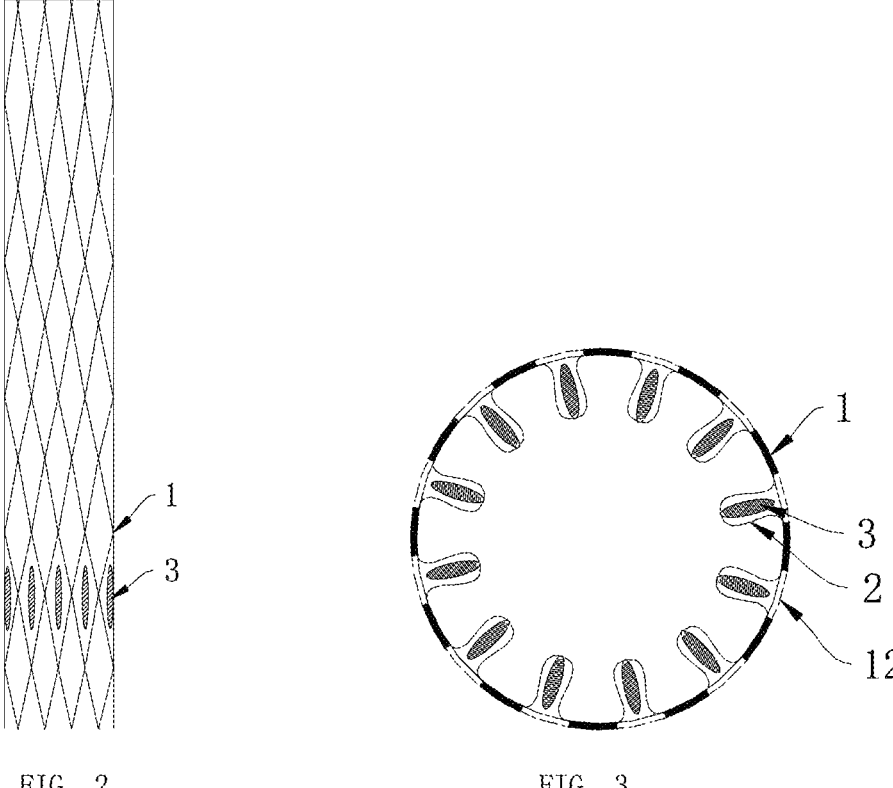
FIG. 2                  FIG. 3

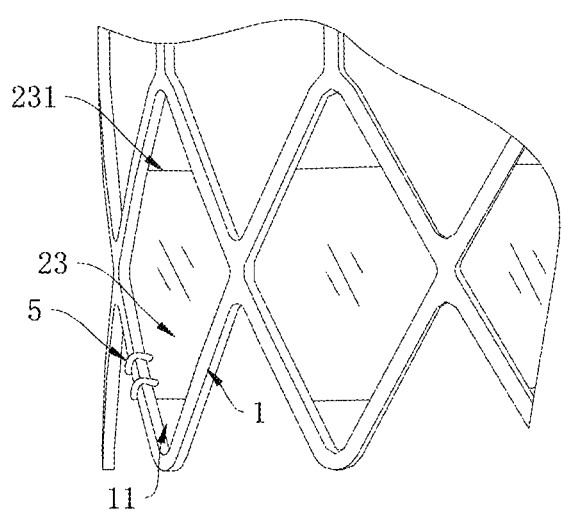
FIG. 17
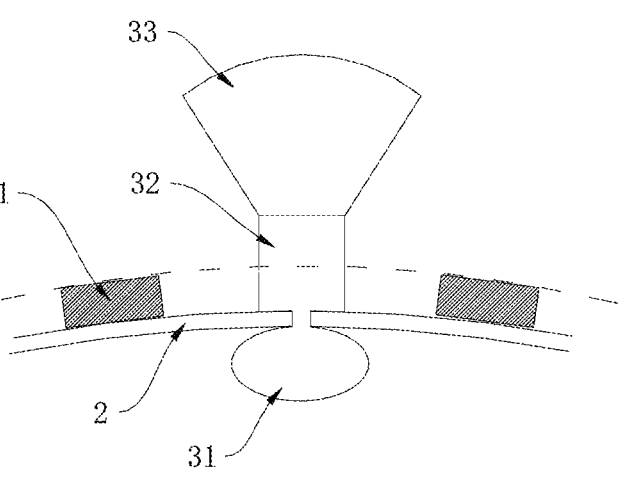
FIG. 18
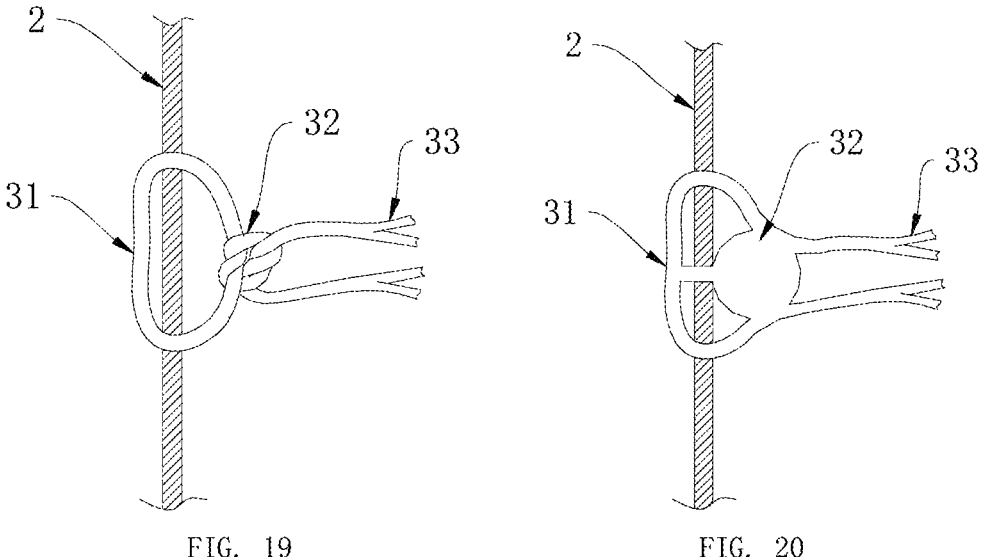
FIG. 19                                    FIG. 20

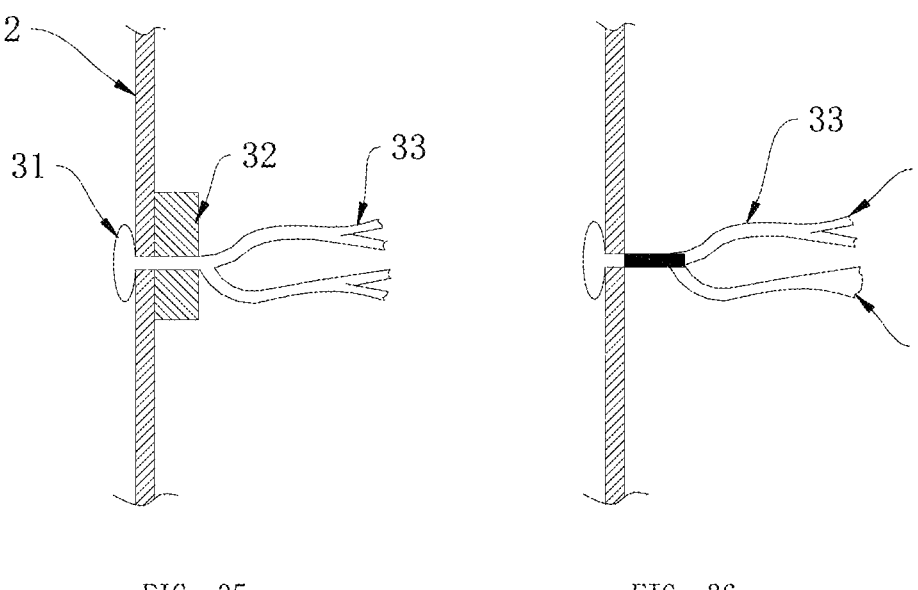
FIG. 35                    FIG. 36
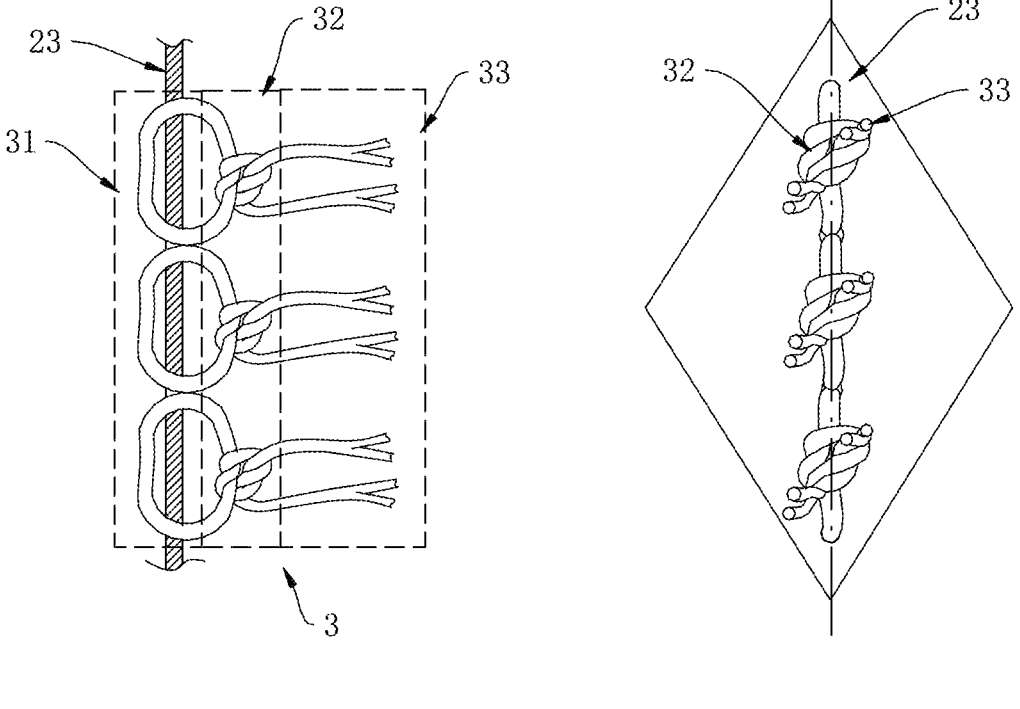
FIG. 37                    FIG. 38

INTERVENTIONAL INSTRUMENT THAT IS CONVENIENT TO POSITION

TECHNICAL FIELD

The present invention relates to the technical field of medical devices, and in particular to an interventional instrument, a processing method and an interventional system.

BACKGROUND

Common interventional instruments, such as valves or vascular stents, are positioned in a blood vessel or organ primarily by the radial supporting force of a metal stent. However, the outer periphery of the metal stent is generally smooth, so once the stent is displaced under the impact of blood flow, not only the performance will be affected, but also potential safety hazards may arise. In some cases where the tissue of the patient adjacent to the implantation site for the interventional instrument suffers from calcification with a poor elasticity, the positioning problem becomes more serious.

In order to solve the positioning problem, in the prior art, an anchor is arranged on the outer periphery of the stent of the interventional instrument for positioning or an attachment is arranged to fill a gap between the stent and the adjacent tissue. However, the anchor may bring a safety hazard, and the attachment may further increase the diameter of the interventional instrument, especially for a self-expandable interventional instrument. An increased diameter makes the loading process more inconvenient and reduces the possibility of the interventional instrument moving smoothly through the human body.

SUMMARY

In order to further improve the positioning effect of the interventional instrument in the human body, and to avoid increasing the loading difficulty of the interventional instrument as much as possible, the present application provides an interventional instrument that facilitates positioning, and a processing method.

The interventional instrument that facilitates positioning according to the present application comprises:

a stent, which has a frame structure with hollowed-out area(s) and has an axis, the stent having a loaded state in which the stent is radially compressed and a released state in which the stent is radially expanded;

a sealing membrane(s), which is connected with the stent and corresponds to at least part of the hollowed-out area(s), wherein in the loaded state, an outer peripheral surface of the stent encloses a receiving space, and the sealing membrane(s) is located in the receiving space; and a friction increasing member(s), which is connected with the sealing membrane(s).

In the following, a number of alternatives are provided, but not as additional limitations to the above-mentioned solution, but merely as further additions or preferences. Without technical or logical contradiction, the alternatives can be combined with the above-mentioned solution independently or in combination.

Optionally, in the released state, the friction increasing member(s) extends outside of the stent for frictional positioning with an adjacent tissue at an implantation site for the interventional instrument.

Optionally, the stent has an axial passage therein, and wherein in the released state, the axial passage is opened, or a leaflet(s) is arranged in the stent for closing or opening the axial passage.

Optionally, the leaflet(s) is an aortic valve, a pulmonary valve, a mitral valve, a tricuspid valve or a venous valve depending on an application site of the interventional instrument, and the stent has a shape adapted to an anatomy of the application site.

Optionally, the stent is a ball-expandable stent or a self-expandable stent.

Optionally, the stent is made by tube cutting or by weaving, or by a combination of the tube cutting and the weaving.

Optionally, the stent is provided with an auxiliary positioning structure for interacting with an adjacent tissue, the auxiliary positioning structure comprising at least one of a group consisting of:

the stent having a corrugated structure that is radially undulated;

the stent being provided with a barb; and the stent being provided with slip resistant texture on an outer surface thereof.

Optionally, the stent is configured to be circumferentially expanded during release, and the sealing membrane is configured to act with the circumferential expansion of the stent to drive the friction increasing member to change a radial position of the friction increasing member.

Optionally, portions of the stent on two sides of the hollowed-out area in a circumferential direction of the stent are linkage sides, and the sealing membrane is at least connected with the linkage sides; and the linkage sides at the two sides of the hollowed-out area are configured to move away from each other during release of the stent to drive the sealing membrane to expand and push the friction increasing member radially outward.

Optionally, the sealing membrane is an inner sealing membrane that contacts an inside of the stent.

Optionally, at least a portion of the sealing membrane is configured as a driving portion corresponding to the hollowed-out area; and the driving portion is configured to be folded in the loaded state, with at least a portion of the friction increasing member surrounded by the folded driving portion.

Optionally, an edge of the driving portion contacts a radial inside of the stent, or the edge of the driving portion contacts an inner edge of the hollowed-out area.

Optionally, in the released state, the sealing membrane(s) is entirely located at a radial inside of the stent.

Optionally, in the released state, the sealing membrane(s) projects beyond the outer peripheral surface of the stent at a position where the friction increasing member is connected.

Optionally, the sealing membranes are spaced apart from each other or the sealing membrane is continuously arranged in a circumferential direction of the stent.

Optionally, the sealing membrane is continuously arranged in the circumferential direction of the stent and is circumferentially closed.

Optionally, the sealing membrane(s) is connected with the stent by sewing or winding.

Optionally, the sealing membrane completely or partially covers the corresponding hollowed-out area.

Optionally, material of the sealing membrane(s) is a biological or artificial membrane, and the sealing membrane(s) covers part of or the entirety of an inside of the stent.

Optionally, the friction increasing member is one or more strands.

Optionally, the strand is a single thread, a cored thread or multi twisted threads.

Optionally, the strand is made of polyester fiber.

Optionally, the strand is a flat strip.

Optionally, the friction increasing member comprises:

an anchor portion connected with the sealing membrane;

a support portion outside the sealing membrane in a radial direction of the stent; and a protrusion portion extending from the support portion towards an outside of the stent for frictional positioning with an adjacent tissue;

wherein the anchor portion, the support portion and the protrusion portion separately use one or more strands, or at least two of the anchor portion, the support portion and the protrusion portion share one strand.

Optionally, depending on an extension path of the strand, both the support portion and the protrusion portion are directly connected with the anchor portion; or one of the support portion and the protrusion portion is directly connected with the anchor portion and the other is indirectly connected with the anchor portion.

Optionally, the friction increasing member(s) comprises a plurality of friction increasing members; and in the released state, the friction increasing members are distributed in a circumferential direction of the stent, and the friction increasing members correspond to the respective hollowed-out areas in position.

Optionally, the friction increasing members are divided into groups in the circumferential direction of the stent, and the adjacent groups are offset from each other in an axial direction of the stent.

Optionally, one axial end of the stent is configured as an inflow end and the other axial end is configured as an outflow end, and the friction increasing members are disposed on a side of the stent adjacent to the inflow end thereof.

Optionally, one or more friction increasing members are disposed within one of the hollowed-out areas.

Optionally, at least a portion of the sealing membrane is configured as a driving portion corresponding to the respective hollowed-out area, and the friction increasing member has an anchor portion and is connected with the driving portion through the anchor portion.

Optionally, the anchor portion passes through the sealing membrane via a connection hole(s), and a part of the anchor portion located inside the sealing membrane prevents the friction increasing member from falling off by limiting the sealing membrane.

Optionally, the anchor portion passes through the sealing membrane via a connection hole, and the part of the anchor portion located inside the sealing membrane is provided with an anchor head which is blocked by the connection hole(s).

Optionally, the anchor head and the rest of the anchor portion are formed in one piece or the anchor head is configured as a limiting part separate from the rest of the anchor portion.

Optionally, the anchor portion is of one or more U-shaped configurations, and wherein two arms of each U-shaped configuration pass through the sealing membrane via respective connection holes, and wherein the two arms meet at a location inside of the driving portion to form a bottom of the U-shaped configuration and are wound together outside of the driving portion to form a support portion, and at least one of the two arms further extends from the support portion to form a protrusion portion.

Optionally, the two arms are wound by forming a knot with each other, or independently from each other, or with other U-shaped configurations outside of the driving portion.

Optionally, the anchor portion vertically passes through the sealing membrane.

Optionally, one anchor portion corresponds to two or more connection holes, and at least two connection holes are distributed in an axial direction of the stent.

Optionally, at least a portion of the sealing membrane is configured as a driving portion corresponding to the hollowed-out area, and wherein one end of the friction increasing member is connected with the driving portion, and the other end is located outside the sealing membrane in a radial direction of the stent and forms a support portion.

Optionally, the friction increasing member further comprises a protrusion portion extending from the support portion towards an outside of the stent for frictional positioning with an adjacent tissue.

Optionally, the friction increasing member is made of a strand, and the support portion is formed by winding the strand; or the friction increasing member is made of a plurality of strands, and the support portion is formed by winding the plurality of strands with each other; and the strand(s) further extends from the support portion to form the protrusion portion.

Optionally, the support portion has a higher rigidity than the protrusion portion.

Optionally, the rigidity of the support portion is improved by locally reinforcing the strand(s).

Optionally, the local reinforcing is selected from at least one of: knotting the strand(s), thickening the strand(s), and modifying the material of the strand(s).

Optionally, the protrusion portion comprises one or more strand sections, and at least one of the strand sections is enlarged in diameter at an end thereof close to the sealing membrane to form the support portion, or at least one of the strand sections has a higher rigidity at an end thereof close to the sealing membrane than at the other end thereof away from the sealing membrane.

Optionally, the support portion is a separate component and is separate from other portions of the friction increasing member.

Optionally, the support portion is a gasket or a sleeve, and the protrusion portion extends through the support portion or abuts against the support portion.

Optionally, the support portions of all the friction increasing members in one hollowed-out area are formed in one piece, or the support portions of the friction increasing members in one hollowed-out area are independent from each other.

Optionally, the support portions of the friction increasing members in different hollowed-out areas are independent from each other.

Optionally, the driving portion is folded, the support portion is surrounded by the folded driving portion and is located in the receiving space.

Optionally, the protrusion portion is a strand section(s) of the strand(s) and/or a coil(s) enclosed by the strand(s).

Optionally, the strand section(s) includes one or a plurality of branched strand sections and the coil(s) includes one or more coils.

Optionally, the strand sections point in the same direction or at least two of the strand sections point in different directions.

Optionally, one end of the thread section away from the support portion is a free end which is further expanded than the rest of the strand section by untwisting or local hot melt deformation.

Optionally, the driving portion is folded, and the protrusion portion is surrounded by the folded driving portion and is located in the receiving space.

The present application further provides a processing method for an interventional instrument, which comprises a stent which has a frame structure with hollowed-out area(s) and has an axis, the stent having a loaded state in which the stent is radially compressed and a released state in which the stent is radially expanded, wherein the processing method comprises the following steps in any order:

step S100, mounting a sealing membrane(s) on the stent, wherein the sealing membrane(s) is connected with the stent and corresponds to at least part of the hollowed-out area(s), wherein in the loaded state, an outer peripheral surface of the stent encloses a receiving space, and the sealing membrane(s) is located in the receiving space, and wherein the sealing membrane(s) is pulled by the stent and thus deformed when state of the stent is changed; and step S200, mounting a friction increasing member(s) on the sealing membrane(s), wherein in the released state, the friction increasing member(s) extends to outside of the stent for frictional positioning with an adjacent tissue at an implantation site for the interventional instrument.

Optionally, in step S100, the sealing membrane(s) is an inner sealing membrane contacting an inside of the stent, and the inner sealing membrane is attached to cover the inside of the stent and sewn and fixed during mounting.

Optionally, in step S200, the friction increasing member is provided as a strand, and during mounting, one end of the strand is inserted through the inner sealing membrane from the outside of the stent into an inside of the stent, then passes through the inner sealing membrane from the other position of the same hollowed-out area back to the outside of the stent, and is knotted with the other portion of the strand outside the stent, with at least one strand section of the knotted strand further extending towards the outside of the stent for frictional positioning with the adjacent tissue.

The present application further provides an interventional system comprising a sheath assembly, a control handle and an interventional instrument, wherein the sheath assembly has opposing distal and proximal ends; the interventional instrument being loaded in the distal end of the sheath assembly, and the control handle being connected with the proximal end of the sheath assembly, and wherein the control handle is operable to release the interventional instrument by driving the sheath assembly, and wherein the interventional instrument is the interventional instrument that facilitates positioning described herein above.

By providing a friction increasing member and improving the mounting portion for the interventional instrument, the interventional instrument according to the present application provides frictional positioning, and also minimizes adverse effects on loading, as well as eliminating as many safety hazards as possible.

BRIEF DESCRIPTION OF THE DRAWINGS

FIG. 1 is a schematic structural view of an interventional instrument in a released state according to an embodiment;

FIG. 2 is a schematic structural view of an interventional instrument in a loaded state according to an embodiment;

FIG. 3 is a schematic cross-section view of an interventional instrument according to an embodiment showing a receiving space;

FIG. 17 is a schematic view showing the distribution of driving portions of an interventional instrument according to an embodiment;

FIG. 18 is a schematic structural view of a friction increasing member of an interventional instrument according to an embodiment;

FIG. 19 is a schematic structural view of a friction increasing member being made of a strand of the interventional instrument according to an embodiment;

FIG. 20 is a schematic structural view of a friction increasing member of an interventional instrument according to an embodiment;

FIG. 35 is a schematic structural view of a support portion of an interventional instrument according to an embodiment;

FIG. 36 is a schematic structural view of a support portion of an interventional instrument according to an embodiment;

FIG. 37 is a schematic structural view of a friction increasing member of an interventional instrument according to an embodiment;

FIG. 38 is a side view of the friction increasing member shown in FIG. 37;

REFERENCE NUMERALS ARE LISTED AS FOLLOWS

Figure 4:
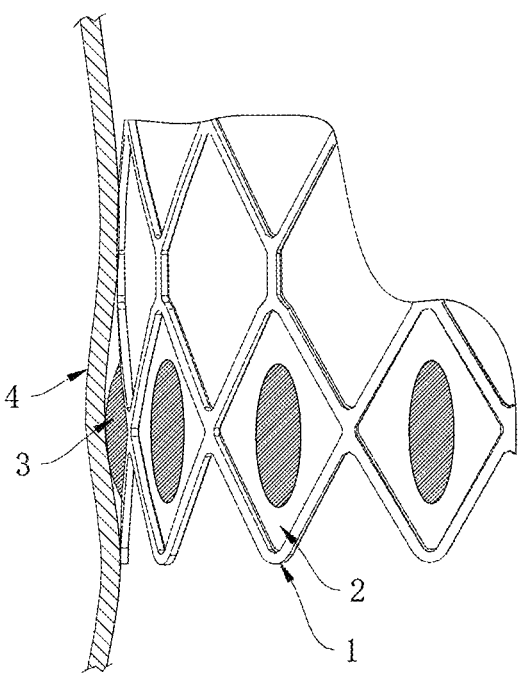
FIG. 4 is a partial schematic view of an interventional instrument in a released state frictionally positioned with an adjacent tissue according to an embodiment.

1, stent; 11, hollowed-out area; 12, boundary of the receiving space; 13, barb; 14, slip resistant texture; 15, corrugated structure; 16, edge of the hollowed-out area;

2, sealing membrane; 21, leaflet; 22, sealing membrane edge; 23, driving portion; 231, driving portion edge; 24, connection hole;

3, friction increasing member; 31, anchor portion; 32, support portion; 33, protrusion portion; 311, two arms of U-shape; 332, untwisted region; 333, hot-melt region;

4, adjacent tissue;

5, binding suture;

6, control handle; 61, catheter;

7, interventional instrument;

8, sheath;

9, core assembly; 91, core tube; 92, locking member; 93, guide head.

DESCRIPTION OF THE EMBODIMENTS

The technical solutions according to the embodiments of the present disclosure will be described in combination with the drawings according to the embodiments of the present disclosure. The described embodiments represent some but not all the possible embodiments.

It should be noted that, when a component is "connected" with another component, it may be directly connected to another component or may be indirectly connected to another component through a further component. When a component is "provided" on another component, it may be directly provided on another component or may be provided on another component through a further component.

Unless otherwise defined, all technical and scientific terms used herein have the same meaning as commonly understood by a person skilled in the art. The terms in the description of the present disclosure are used to describe specific embodiments, and not to limit the present disclosure. The term "and/or" used herein includes any combinations of one or more of the listed options, as well as the combination of all of the listed options.

Referring to FIGS. 1 to 4, in one embodiment of the present application, an interventional instrument that facilitates positioning is provided and includes:

A stent 1, which has a frame structure with hollowed-out area(s) 11 and has an axis, also has a loaded state (as shown in FIG. 2), in which the stent is radially compressed, and a released state (as shown in FIG. 1), in which the stent is radially expanded;

A sealing membrane(s) 2, which is connected with the stent 1 and the position of which corresponds to at least part of the hollowed-out area(s) 11, and in the loaded state, the outer peripheral surface of the stent 1 encloses a receiving space, and the sealing membrane(s) 2 is located in the receiving space; and A friction increasing member(s) 3, which is connected with the sealing membrane(s) 2.

In the present application, the stent 1 can use conventional techniques with a radially compressible structure for easy loading and delivery of the same, and can be released by means of balloon dilatation or based on the flexibility thereof after reaching a desired position in the human body. Here, the end of the stent 1 close to the operator is designated as the proximal end and the end thereof close to the lesion and entering the human body is designated as the distal end.

The sealing membrane 2 can be made of biocompatible material and at least cover part of the corresponding hollowed-out area(s) 11. In order to avoid increasing the loading difficulty of the stent 1, the sealing membrane(s) 2 is located in the receiving space in the loaded state. Illustratively, the outer ring shown in FIG. 3 is the boundary of the receiving space 12, and the sealing membrane(s) 2 is folded in the space enclosed by the boundary of the receiving space 12 and does not extend to the outside of the boundary of the receiving space 12, without affecting the outer diameter of the stent 1. In the released state, the relative relationship between the sealing membrane 2 and the stent 1 in the radial direction is not strictly limited, the sealing membrane 2 can be located inside the stent, or flush with the side wall of the stent in the radial direction, or even partially protrude from the outside of the stent.

The friction increasing member(s) 3 is connected with the sealing membrane(s) 2. In the loaded state, the friction increasing member(s) 3 can extend into the receiving space along with the sealing membrane(s) 2. Since part of the, or even the entire, friction increasing member 3 is located in the receiving space, the influence from the friction increasing member 3 on the peripheral dimension of the stent can be reduced, with the loading difficulty reduced as much as possible, which is a key point for the self-expandable stent.

In the present application, the friction increasing member(s) 3 is connected with the sealing membrane(s) 2, so that the friction increasing member(s) 3 is allowed to enter the receiving space in the loaded state. During loading, even though it is possible that part of the friction increasing member can be located outside the stent due to improper operation, there is still the possibility or ability for the friction increasing member to enter the receiving space.

The friction increasing member 3 can be made of biocompatible material. In order to facilitate the movement of the friction increasing member(s) 3 along with the sealing membrane(s) 2 when the stent 1 transitions from the loaded state to the released state, the friction increasing member 3 is preferably provided with elasticity, in such a way that the friction increasing member 3 can closely contact and tension an adjacent tissue 4 in the released state. In a preferred embodiment, the friction increasing member 3 in the released state is extended to the outside of the stent for frictional positioning with the adjacent tissue 4 at the implantation site for the interventional instrument.

In order to allow the friction increasing member(s) 3 in the loaded state to extend into the receiving space along with the sealing membrane(s) 2, the direct connecting portions between the friction increasing member 3 and the stent 1 should be reduced so as to avoid restriction on the freedom of the friction increasing member 3. In the released state, the friction increasing member 3 extends to the outside of the stent. As shown in FIG. 4, the friction increasing member 3 is sandwiched or tensioned between the stent 1 and the adjacent tissue 4, thereby increasing the friction and thereby further improving the positioning effect.

The stent 1 generally has the shape of a meshed cylinder and is made of stainless steel or nickel-titanium alloy. The interior of the stent 1 has an axial passage. In various embodiments, the axial passage in the released state can be kept open, or leaflet(s), such as leaflet(s) 21 shown in FIG. 1, can be provided within the stent 1 for closing or opening the axial passage.

In the case where the interventional instrument only plays a supporting role and does not need to control and interfere with the blood flow, the axial passage in the released state can always be open. In the case where the direction of the blood flow needs to be controlled, for example, to prevent backflow, leaflet(s) can be provided in the stent. Generally, one single leaflet, two leaflets or three leaflets can be fixed in the stent by means of suturing or bonding to interfere with the opening or closing of the axial passage.

The shape(s) and function(s) of the leaflet(s) can be configured depending on the implantation site for the interventional instrument. In various embodiments, depending on the implantation site for the interventional instrument, the leaflet(s) can be used to form an aortic valve, a pulmonary valve, a mitral valve, a tricuspid valve or a venous valve, respectively, and the stent has a shape adapted to the anatomy at the implantation site.

Figure 5:
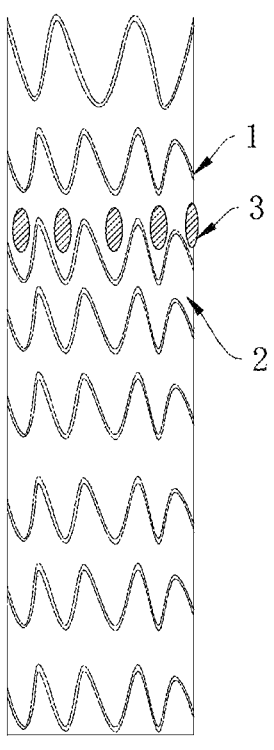
FIG. 5 is a schematic structural view of an interventional instrument as a vascular stent according to an embodiment.

Depending on the implantation site for the interventional instrument, the stent has a shape adapted to the surrounding tissue. For example, in the case where the interventional instrument is implanted at the aortic valve, the stent 1 and the leaflet(s) 21 are adapted thereto, as shown in FIG. 1. As a further example, the stent 1 as shown in FIG. 5 is a vascular stent, the inside of the stent 1 is covered with a sealing membrane(s) 2, and a friction increasing member(s) 3 is provided on the sealing membrane(s) 2.

The present application is not focused on the improvement of the stent and leaflet(s). Although improved or preferred stent and leaflet(s) are provided in the following embodiments, alternative stent and leaflet(s) using conventional techniques can also be used.

Depending on the manner in which the stent is released in the human body, in one embodiment, the stent is a ball-expandable stent, and in a preferred embodiment, the stent is a self-expandable stent. For a self-expandable stent, which has a limited loading space, it is more sensitive to the changes of the outer diameter when loading the stent. In a traditional technique, a covering is always provided on the outer periphery of the stent to increase the friction, which will inevitably increase the outer diameter in the loaded state, thereby making the loading process inconvenient, greatly reducing the flexibility of the loading portion of the stent, and making it difficult to pass through the complex paths in the human body. Therefore, the advantages brought by the friction increasing member(s) to the self-expandable stent are more prominent than the ball-expandable stent.

Figure 6:
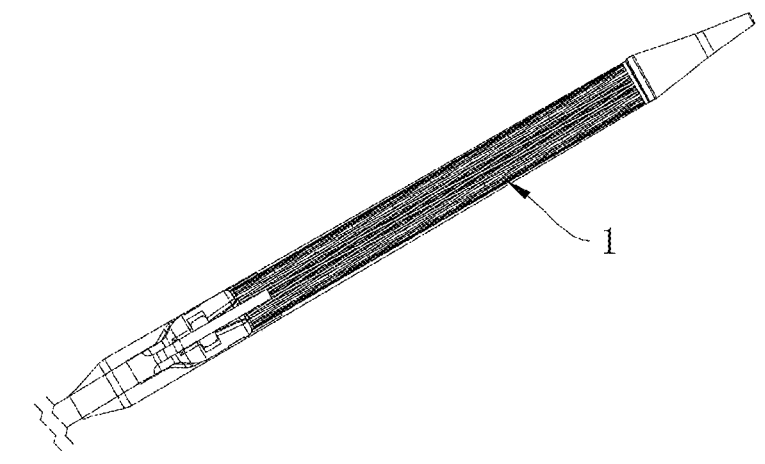
FIG. 6 is a schematic structural view of an interventional instrument according to an embodiment processed by cutting a tube.

In various embodiments, the stent can be substantially made by tube cutting or by weaving, or by combining tube cutting and weaving. Referring to FIG. 6, in one embodiment, the stent 1 is substantially made by tube cutting. The stent 1 shown in FIG. 6 is in a loaded state, and a radial gap is formed between the inside of the radially compressed stent 1 and a sheath core of a delivery system, in which the sealing membrane and (at least a part of) the friction increasing member according to the present application are received.

In order to further improve the positioning effect, in addition to the friction increasing member, the stent can be further improved in various embodiments.

Figure 7:
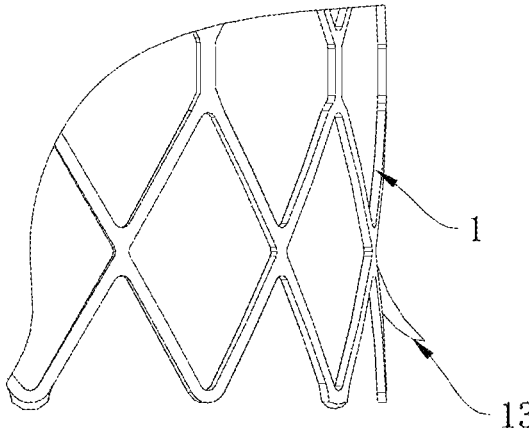
FIG. 7 is a schematic structural view of an interventional instrument according to an embodiment with a barb provided on a stent.

Referring to FIG. 7, in one embodiment, the stent 1 is provided with an auxiliary positioning structure for interacting with the adjacent tissue. Here, the auxiliary positioning structure is configured as barb 13 provided on the stent 1. A plurality of barbs 13 can be provided along the circumferential direction of the stent 1. In the released state, the barb 13 can anchor into the adjacent tissue, thereby preventing displacement of the interventional instrument.

Figure 8:
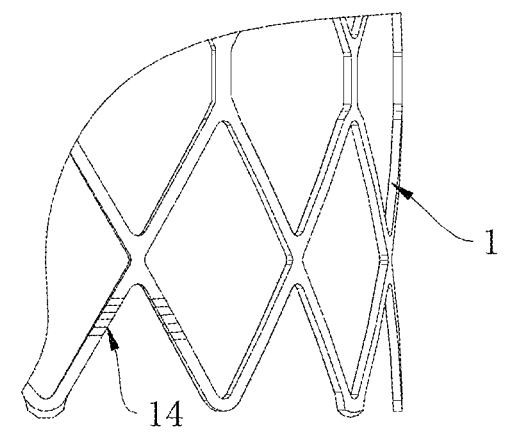
FIG. 8 is a schematic structural view of an interventional instrument according to an embodiment with slip resistant textures provided on a stent.

Referring to FIG. 8, in one embodiment, the stent 1 is provided with an auxiliary positioning structure for interacting with the adjacent tissue. Here, the auxiliary positioning structure is configured as slip resistant texture 14 provided on the stent 1. The slip resistant texture 14 can be provided along part or the entire of the circumference of the stent 1 and along at least one axial section of the stent 1. The slip resistant texture 14 can be processed during the cutting process of the stent. In the released state, the slip resistant texture 14 functions to act on the adjacent tissue to increase friction, thereby preventing displacement of the interventional instrument.

Figure 9:
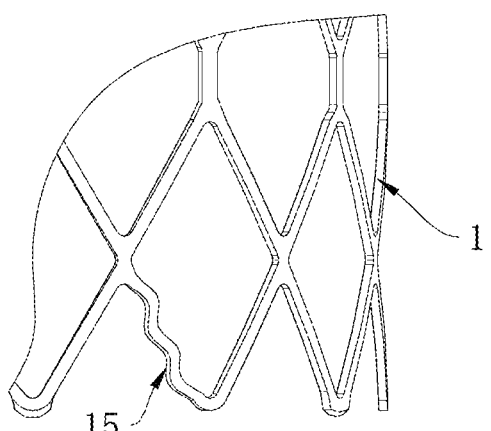
FIG. 9 is a schematic structural view of an interventional instrument according to an embodiment with a corrugated structure provided on a stent.

Referring to FIG. 9, in one embodiment, the stent 1 is provided with an auxiliary positioning structure for interacting with the adjacent tissue. Here, the auxiliary positioning structure is configured as corrugated structure 15 provided on the stent 1. The corrugated structure 15 has at least a radial undulation, which can be provided along part or the entire of the circumference of the stent 1 and along at least one axial section of the stent 1. The corrugated structure 15 can be made by heat setting. In the released state, the corrugated structure 15 can act on the adjacent tissue to increase friction, thereby preventing displacement of the interventional instrument.

When the stent transitions from the loaded state to the released state, the sealing membrane(s) moves with the stent and provides radially outward expansion force to the friction increasing member(s) so that the friction increasing member(s) abuts outwardly against the adjacent tissue, thereby obtaining sufficient friction. The material of the sealing membrane is biologic or artificial membrane, and covers part or the entire of the inside of the stent.

In the case of artificial membrane, it is preferable to use a woven membrane as the artificial membrane. Since the woven membrane has interstices between fibers, the friction increasing member can directly or indirectly pass through the interstices between fibers, thereby reducing damage to the structure of the woven membrane and avoiding tearing the sealing membrane due to local damage or stress concentration when the friction increasing member pulls the sealing membrane. In particular, the woven membrane can be woven using traditional techniques.

Figure 10:
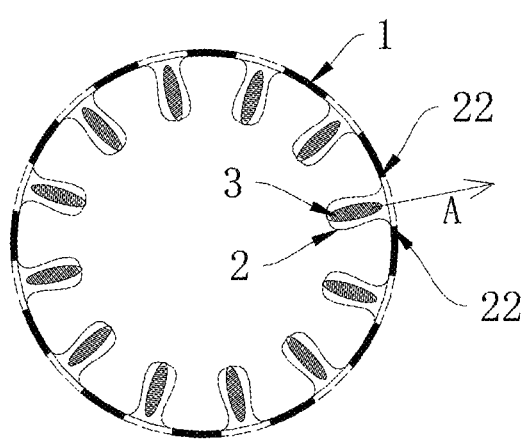
FIG. 10 is a schematic view showing the principle of the sealing membrane driving the friction increasing member of the interventional instrument.

Referring to FIG. 10, in one embodiment, the stent 1 is circumferentially expanded when released, and the sealing membrane(s) 2 acts with the circumferential expansion of the stent 1 to drive the friction increasing member(s) 3 to change the radial position.

In one hollowed-out area, the portions of the stent 1 on two sides of the hollowed-out area in the circumferential direction of the stent are linkage sides, and the sealing membrane 2 is at least connected with the linkage sides. As shown in FIG. 10, the sealing membrane edges 22 of the sealing membrane 2 at the two sides in the circumferential direction of the stent are fixedly connected with the linkage sides of the stent 1. During the release of the stent 1, the linkage sides on the two sides of the hollowed-out area move away from each other in such a way that the stent 1 is circumferentially expanded and thus tightens the sealing membrane(s) 2, so that the friction increasing member(s) 3 which is connected with the sealing membrane(s) 2 moves radially outward in the direction indicated by arrow A until it abuts against the adjacent tissue.

Depending on the position of the sealing membrane(s) relative to the stent in the radial direction, the sealing membrane(s) can have different configurations. Referring to FIG. 10, in one embodiment, the sealing membrane 2 is configured as an inner sealing membrane against the inside of the stent. In the loaded state, the sealing membrane 2 is at least partially folded, and at least a portion(s) of the friction increasing member(s) 3 is surrounded by the folded portion(s) of the sealing membrane 2.

As the sealing membrane 2 is entirely received in the receiving space, the friction increasing member(s) 3 can also be entirely received in the receiving space if the friction increasing member(s) 3 is totally surrounded by the folded portion(s) of the sealing membrane 2. Alternatively, a portion(s) of the friction increasing member(s) 3 is surrounded by the folded portion(s) of the sealing membrane 2, while the other portion(s) of the friction increasing member(s) 3 extends slightly outside the stent. However, it should be noted that the other portion(s) of the friction increasing member(s) 3 outside the stent only occupies a small portion of the friction increasing member(s) 3, so that the difficulty of loading the interventional instrument would not be significantly increased.

In the case where the sealing membrane has a large area, it will inevitably cover the frame bar(s) of the stent while covering a part of the hollowed-out area(s) in the stent. When the sealing membrane is connected to the stent, it is usually sewn to the frame bar(s) of the stent. In a preferred embodiment, in order to reduce changes of the radial dimension, at least part of the sealing membrane is configured as a driving portion(s) corresponding to the hollowed-out area(s), to which the friction increasing member(s) is connected. In the loaded state, the driving portion(s) is folded and at least a portion(s) of the friction increasing member(s) is surrounded by the folded driving portion(s).

Figure 11:
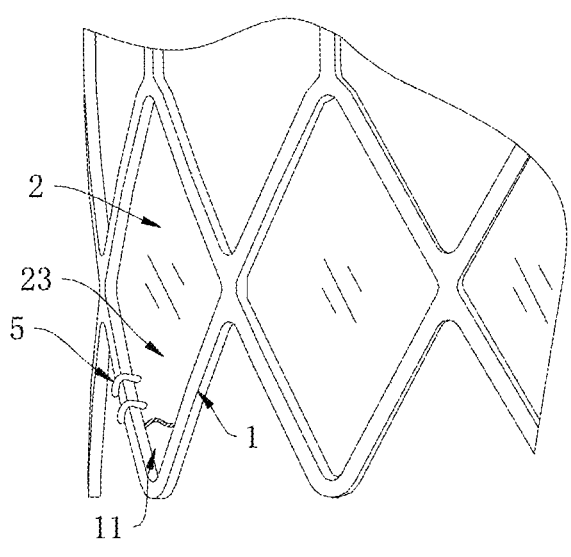
FIG. 11 is a schematic view showing the radial positional relationship between the sealing membrane and the stent according to an embodiment.

Referring to FIG. 11, in one embodiment, the stent 1 is provided with a plurality of hollow-out areas 11, and the sealing membrane 2 is configured as an inner sealing membrane covering the inside of the stent 1. The sealing membrane 2 is sewn to the frame bar(s) of the stent 1 by a binding suture(s) 5 (only part of the binding suture(s) is shown in the figure), and a portion of the sealing membrane 2 corresponding to one of the hollowed-out areas shown in the figure is a driving portion 23. The friction increasing member (not shown) is provided on the driving portion 23. It should be noted that only a part of the stent is shown in the figure, and the position and number of the friction increasing member(s) can be provided as required. Since the sealing membrane 2 is configured as an inner sealing membrane, the edges of the driving portion 23 in this embodiment contact the radial inside of the stent.

Figure 12:
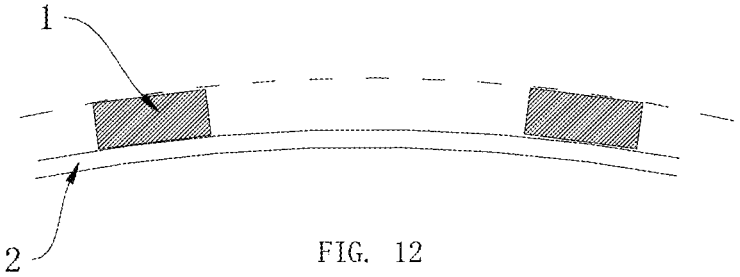
FIG. 12 is a schematic view showing the radial positional relationship between the sealing membrane and the stent of the interventional instrument according to an embodiment.

Referring to FIG. 12, in another embodiment, the stent 1 is provided with a plurality of hollowed-out areas 11, and sealing membranes 2 are spaced apart from each other. The driving portions 23 corresponding to the respective hollowed-out areas 11 are independent from each other. Binding sutures 5 (only part of the binding sutures is shown) are respectively sewn to the frame bar(s) of the stent 1. It should be noted that the driving portion 23 in this embodiment does not contact the inside of the frame, but rather the edges of the driving portion 23 contact the edges of the hollowed-out areal 6.

Figure 13:
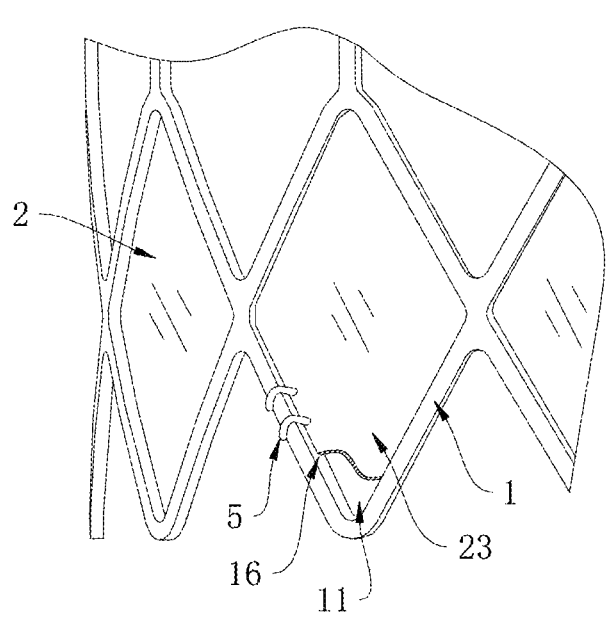
FIG. 13 is a schematic view showing the radial positional relationship between the sealing membrane and the stent of the interventional instrument according to an embodiment, relative to that shown in FIG. 11.
Figure 14:
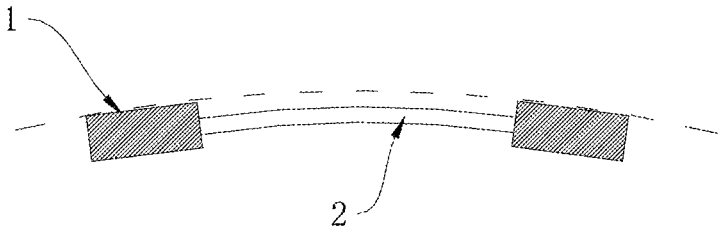
FIG. 14 is a schematic view showing the radial positional relationship between the sealing membrane and the stent of the interventional instrument according to an embodiment, relative to that shown in FIG. 12.

FIGS. 13 and 14 further show the relationship between the sealing membrane and the stent in the radial direction, and the detailed description related thereto is the same as that described above in connection to FIGS. 11 and 12.

Figure 15:
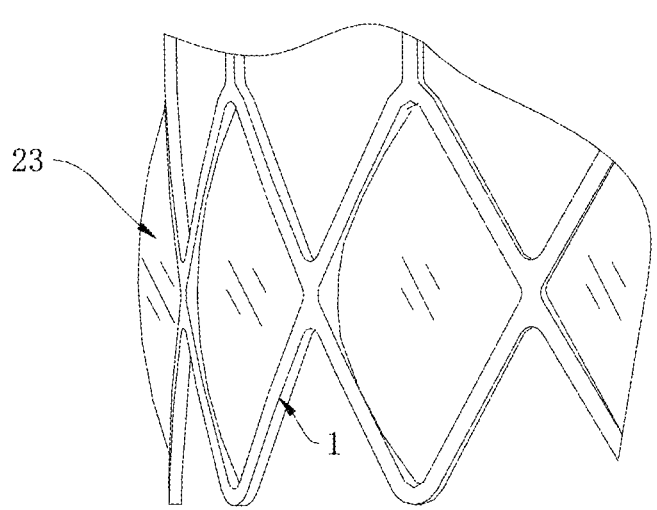
FIG. 15 is a schematic view showing the sealing membrane of the interventional instrument protruding beyond the stent.

Referring to FIG. 11, in various embodiments, the sealing membrane 2, which is tensioned in the released state, is entirely located at the radial inside of the stent. Referring to FIG. 15, in another embodiment, the sealing membrane 2 in the released state projects from the outer peripheral surface of the stent at the position where the friction increasing member is connected (the driving portion 23).

The stent may be provided with multiple covering films. In a preferred embodiment, all the covering films provided on the stent use the sealing membrane as described above.

Figure 16:
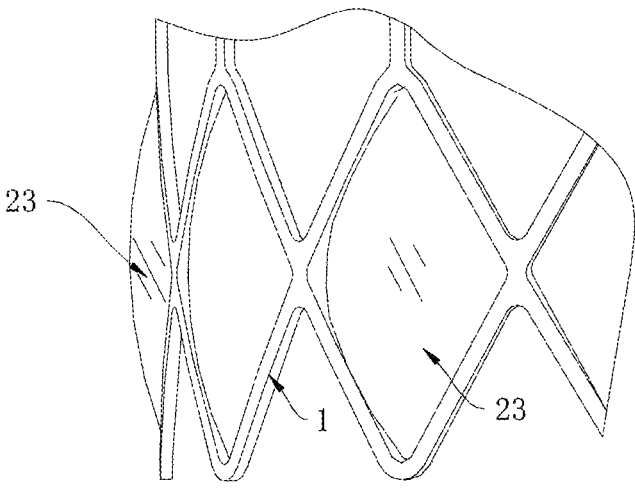
FIG. 16 is a schematic view showing the distribution of driving portions of an interventional instrument according to an embodiment.

The sealing membrane can be provided on the stent at different locations in the axial and circumferential direction of the stent. In various embodiments, sealing membranes can be spaced apart from each other in the circumferential direction of the stent or a sealing membrane can be continuously arranged in the circumferential direction of the stent. For example, as shown in FIG. 11, the sealing membrane 2 is continuously arranged in the circumferential direction of the stent 1. For another example, as shown in FIG. 16, the sealing membranes are spaced apart from each other in the circumferential direction of the stent 1, and the driving portions 23 are provided at every other cell.

In a preferred embodiment, the sealing membrane is continuously arranged in the circumferential direction of the stent and is circumferentially closed so that the connection and the strength thereof can be secured and good sealing effect can be obtained.

In various embodiments, the sealing membrane completely or partially covers the corresponding hollowed-out area(s). For example, as shown in FIGS. 11 and 12, the sealing membrane 2 completely covers the corresponding hollowed-out area(s) 11.

In another embodiment, for example, as shown in FIG. 17, the stent 1 has a plurality of hollowed-out areas 11. The sealing membrane 2 is configured as an inner sealing membrane covering the inside of the stent 1. The sealing membrane 2 is sewn on the frame bar(s) of the stent 1 through binding suture(s) 5 (only part of the binding suture(s) is shown in the figure). The portion of the sealing membrane 2 corresponding to one of the hollowed-out areas in the figure is configured as one driving portion 23. The friction increasing member (not shown) is arranged on the driving portion 23. However, the driving portion 23 does not completely cover the corresponding hollowed-out area 11, while the driving portion edges 231 are still located in the hollowed-out area 11. Since two sides of the driving portion 23 in the circumferential direction are fixed to the stent 1, the driving portion 23 can still function to drive the friction increasing member to change the radial position.

In order to facilitate the processing and to ensure the safety of the material, in a preferred embodiment, the friction increasing member 3 is configured as one or more strands.

The present application is not focused on the improvement of the strand. For example, in various embodiments, the strand can include a single thread, a cored thread or multi twisted threads. Considering the specific application environments and performance requirements, the surface of the strand should have a certain roughness, which can be achieved by the surface treatment of the strand or selecting a suitable material. In a preferred embodiment, the strand is made of polyester fiber.

As the friction increasing member, the strand itself has a certain elasticity. Therefore, it is particularly suitable for the interventional instrument to be used in the living body as the tissue (if no obvious calcification) surrounding the interventional instrument also has a certain elasticity so that the tissue is self-deformable to adapt to the friction increasing member. Common applications such as aortic valves have a relatively smooth inner periphery which is prone to peripheral leakage. The interventional instrument with the friction increasing member according to the present invention not only further facilitates the positioning effect, but also directly or indirectly reduces the risk of peripheral leakage.

Fixing the strands by winding is a simple and easy method, and any additional connections or locks can be omitted. The cross-sectional shape of the strand has an influence on the winding and fixing of the strands. In a preferred embodiment, the strand is configured as a flat strip.

In order to facilitate the connection between the friction increasing member and the sealing membrane and to fully exert the friction increasing effect of the friction increasing member, see FIG. 18, where the friction increasing member 3 includes an anchor portion 31 connected to the sealing membrane 2, a support portion 32 outside the sealing membrane 2 in the radial direction of the stent 1, and a protrusion portion 33 extending from the support portion 32 towards the outside of the stent 1 for frictional positioning with the adjacent tissue.

Referring to FIG. 19 and the description about the strand above, it can be seen that the anchor portion 31, the support portion 32, and the protrusion portion 33 all use a strand. Since the strands are easy to be wound, overlapped and connected with each other, the number of strands of the friction increasing member 3 is not strictly limited. For example, the anchor portion 31, the support portion 32, and the protrusion portion 33 can each independently use one or more strands, or at least one strand is shared between two of them. In addition, the figures shown are only for illustrating the principle, and the specific threading method of the strand with respect to the sealing membrane 2 is not strictly limited.

Referring to FIG. 20, depending on the extension path of the strand, in one embodiment, both the support portion 32 and the protrusion portion 33 are directly connected with the anchor portion 31. As shown in the figure, the specific winding method of the support portion 32 is omitted, and the support portion 32 can be formed by locally adhering or thermally fusing.

Figure 21:
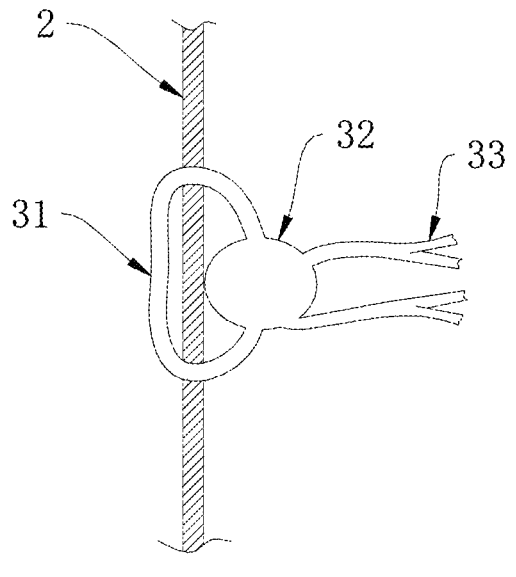
FIG. 21 is a schematic structural view of a friction increasing member of an interventional instrument according to an embodiment.

Referring to FIG. 21, depending on the extension path of the strand, in one embodiment, the support portion 32 is directly connected with the anchor portion 31 and the protrusion portion 33 is indirectly connected with the anchor portion 31 through the support portion 32. As shown in the figure, the specific winding method of the support portion 32 is omitted, and the support portion 32 can be formed by locally adhering or thermally fusing.

Figure 22:
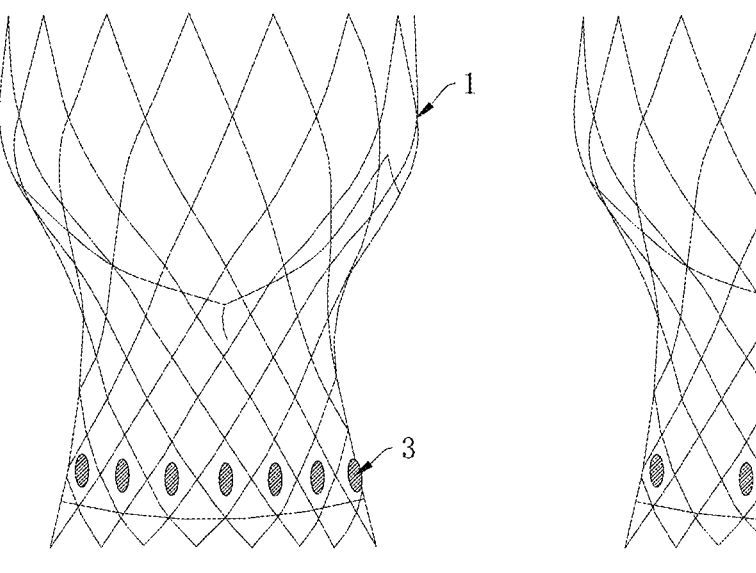
FIG. 22 is a schematic structural view showing the distribution of the friction increasing members of the interventional instrument according to an embodiment.

Referring to FIG. 22, in one embodiment, the stent 1 is covered with an inner sealing membrane, and a plurality of friction increasing members 3 are provided on the inner sealing membrane. In the released state, the friction increasing members 3 are distributed along the circumferential direction of the stent 1, and the friction increasing members 3 correspond to the respective hollowed-out areas. In a circle of the hollowed-out areas of the stent 1, the inner sealing membrane is provided with friction increasing members 3 corresponding to each of the hollowed-out areas in the circle, which can be considered to be distributed continuously in the circumferential direction.

Figure 23:
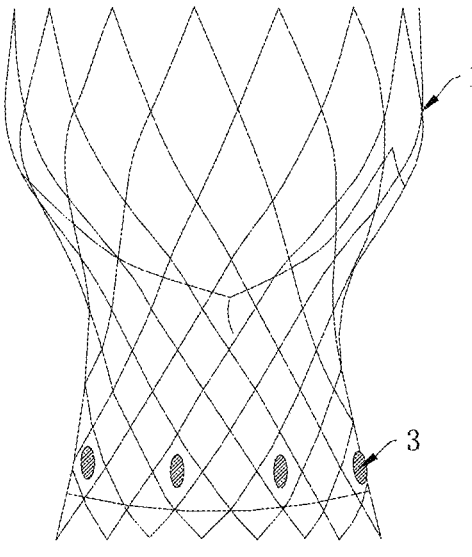
FIG. 23 is a schematic diagram showing the distribution of the friction increasing members of the interventional instrument according to an embodiment.

Referring to FIG. 23, in one embodiment, the stent 1 is covered with an inner sealing membrane, and a plurality of friction increasing members 3 are provided on the inner sealing membrane. In the released state, the friction increasing members 3 are distributed along the circumferential direction of the stent 1, and the friction increasing members 3 correspond to the respective hollowed-out areas. In a circle of the hollowed-out areas of the stent 1, the inner sealing membrane is provided with friction increasing members 3 corresponding to every other hollowed-out area in the circle, which can be considered to be distributed at intervals in the circumferential direction.

Figure 24:
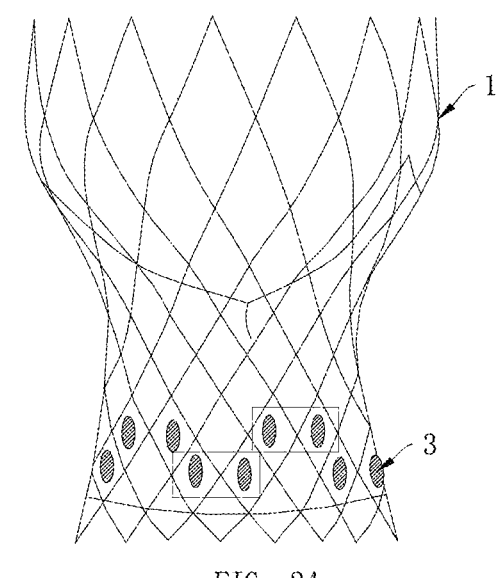
FIG. 24 is a schematic diagram showing the distribution of the friction increasing members of the interventional instrument according to an embodiment.

Referring to FIG. 24, in one embodiment, the stent 1 is covered with an inner sealing membrane, and a plurality of friction increasing members 3 are provided on the inner sealing membrane. The friction increasing member 3 are divided into multiple groups along the circumferential direction of the stent. As shown in the figure, two friction increasing members 3 in one box can be regarded as one group of friction increasing members 3, and the adjacent groups of friction increasing members 3 are offset from each other in the axial direction of the stent; that is, the axial positions of the adjacent boxes are different, in such a way that the adjacent groups of friction increasing members 3 are offset from each other in the axial direction during loading, thereby avoiding mutual squeeze and interference therebetween.

When the interventional instrument is implanted in the blood flow, the side thereof adjacent to the inflow end is first subject to the impact of the blood flow. In a preferred embodiment, the stent 1 has an inflow end at one axial end and an outflow end at the other end, and the friction increasing member 3 is provided on the side of the stent 1 adjacent to the inflow end (referring to FIGS. 22 to 24 or other relevant figures).

In one hollowed-out area, one or more friction increasing members can be provided. In the case where a plurality of friction increasing members are provided, the friction increasing members can be provided along the circumferential direction or the axial direction of the stent, preferably along the axial direction, and are independent from each other.

Figure 25:
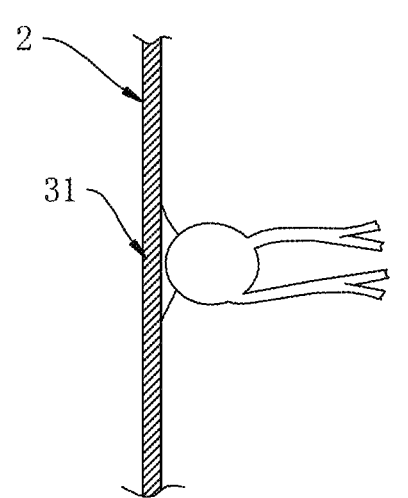
FIG. 25 is a schematic view of a connected anchor head of an interventional instrument according to an embodiment.

At least a part of the sealing membrane is configured as a driving portion corresponding to the hollowed-out area, and the friction increasing member has an anchor portion and is connected with the driving portion via the anchor portion. The anchor portion primarily functions to provide a connection portion for fixing with the sealing membrane, thereby preventing the friction increasing member 3 from falling off. The anchor portion can be fixed against the outside of the sealing membrane. As shown in FIG. 25, in an interventional instrument according to one embodiment, the stent 1 is covered with a sealing membrane 2, the anchor portion 31 of the friction increasing member is fixed against the outside of the sealing membrane 2, and the rest of the friction increasing member extends radially outwardly from the anchor portion 31.

Figure 26:
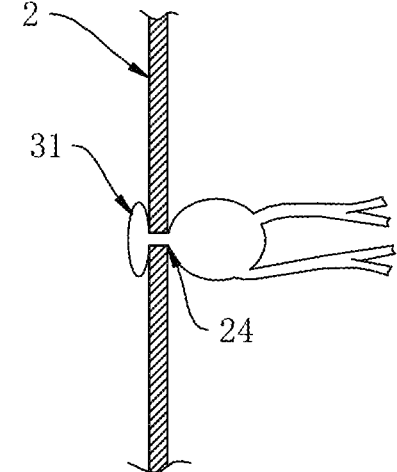
FIG. 26 is a schematic view of a connected anchor head of an interventional instrument according to an embodiment.

In another embodiment, referring to FIG. 26, the anchor portion 31 passes through the sealing membrane 2 via connection hole 24 to provide a better connection and increase the strength of the connection. One anchor portion 31 corresponds to one to three connection holes. The embodiments corresponding to one to three connection holes can be referred to in FIG. 26, FIG. 21 and FIG. 20, respectively.

The anchor portion 31 shown in FIG. 21 is substantially U-shaped and passes through the sealing membrane 2 through two connection holes. The anchor portion 31 shown in FIG. 20 is substantially W-shaped (or considered as two locally merged U-shapes) and passes through the sealing membrane 2 through three connection holes.

The anchor portion 31 preferably passes vertically through the sealing membrane 2, so as to avoid the risk of tearing the sealing membrane 2 caused by the anchor portion 31 passing obliquely through the sealing membrane 2, especially when the sealing membrane 2 has a certain thickness because the effect is more prominent.

The anchor portion 31 passes through the sealing membrane 2 via the connection hole(s) 24, and the portion of the anchor portion 31 inside the sealing membrane 2 prevents the friction increasing member from falling off the sealing membrane 2. In FIG. 26, the portion of the anchor portion 31 inside the sealing membrane 2 is provided with an anchor head that is blocked by the connection hole 24, and the anchor head is configured as an enlarged portion that can be blocked by the connection hole 24. The anchor head and the rest of the anchor portion 31 can be formed in one piece or the anchor head can be independently provided as a limiting part.

Figure 27:
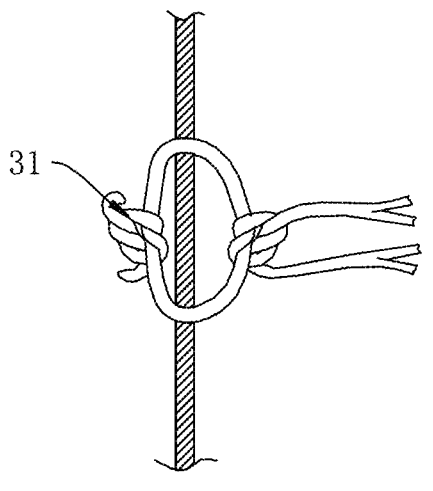
FIG. 27 is a schematic view of a connected anchor head of an interventional instrument according to an embodiment.

The anchor head and the strand can be formed in one piece. For example, in one embodiment, the anchor head is formed by knotting the strand, see FIG. 27. In another embodiment, the anchor head can be a limiting part connected with the strand.

Figure 28:
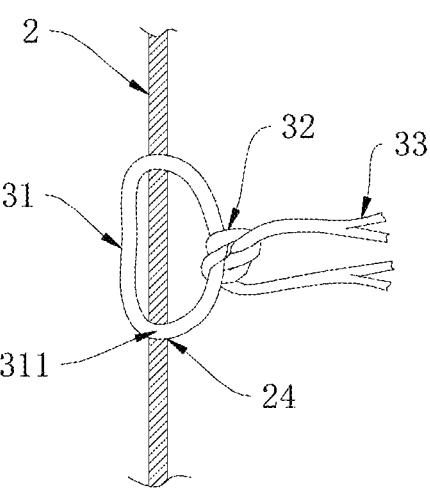
FIG. 28 is a schematic structural view of a friction increasing member of an interventional instrument according to an embodiment.
Figure 29:
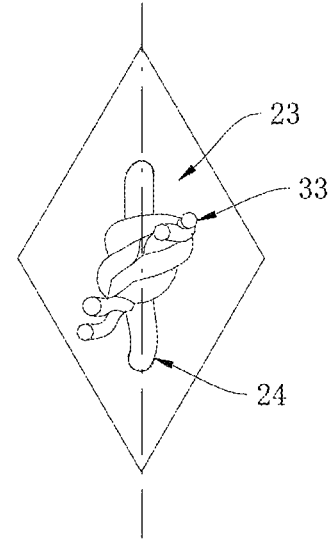
FIG. 29 is a side view of the friction increasing member shown in FIG. 28.

Referring to FIGS. 28 and 29, in one embodiment, the anchor portion 31 is U-shaped. Two arms 311 of the U-shaped anchor portion 31 pass through the sealing membrane 2 via the respective connection holes 24, wherein the two arms 311 of the U-shaped anchor portion 31 meet at the inside of the driving portion of the sealing membrane 2 to form the bottom of the U-shaped anchor portion 31, and the two arms 311 of the U-shaped anchor portion 31 wind with each other at the outside of the driving portion of the sealing membrane 2 to form the support portion 32. At least one of the two arms 311 of the U-shaped anchor portion 31 further extends from the support portion 32 to form the protrusion portion 33.

In the present embodiment, the friction increasing member can generally use one or more strands, preferably one strand which facilitates the processing and avoids redundant connecting operations. The U-shaped anchor portion 31 corresponds to two connection holes 24. In order to avoid axial pulling of the friction increasing member when the sealing membrane 2 is folded in the circumferential direction, the two connection holes 24 are provided in the axial direction of the stent.

In the case where one anchor portion 31 corresponds to two or more connection holes 24, at least two or all of the connection holes 24 are provided in the axial direction of the stent. Preferably, all the connection holes 24 in the same driving portion are provided in the axial direction of the stent (the figure can be considered as in the expanded state).

The two arms 311 of the U-shaped anchor portion 31 are wound by knotting with each other or independently from each other at the outside of the driving portion 23. The knotting method should at least prevent the two arms 311 from being loosened easily. For example, the two arms 311 can be wound and knotted with each other at least twice, and after that, a proper tightening can be made, thereby forming the support portion 32 at the knotted portion, which can reduce shaking of the protrusion portion 33 in the released state and provide sufficient tension on the adjacent tissue.

In order to provide better contact and maintain the required interaction between the friction increasing member and the surrounding adjacent tissue, in one embodiment, at least a portion of the sealing membrane is configured as a driving portion corresponding to the hollowed-out area, one end of the friction increasing member is connected to the driving portion, and the other end extends radially outside the sealing membrane of the stent and forms the support portion. After the stent is released, the support portion can extend radially outwardly through its own elasticity or by restoring its presetting shape.

In order to further enlarge that contact area with the adjacent tissue, in another preferred embodiment, the friction increasing member further includes a protrusion portion extending from the support portion toward the outside of the stent for frictional positioning with the adjacent tissue.

In order to better support the protrusion portion, the support portion has a higher rigidity than the protrusion portion. For example, in the case where the friction increasing member uses strand, the strand can be locally reinforced to improve the rigidity of the support portion. This method can be used in the case where the protrusion portion is formed by direct extension of the anchor portion, and the rigidity can be improved by means of a modification of the strand itself or by means of additional components.

Figure 30:
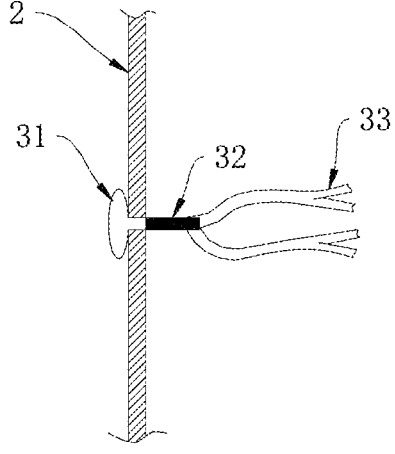
FIG. 30 is a schematic structural view of a support portion of an interventional instrument according to an embodiment.

Referring to FIG. 30, in one embodiment, the interventional instrument includes a stent, a sealing membrane 2 covering the stent, and a friction increasing member distributed on the sealing membrane 2. The friction increasing member is configured as a strand, including an anchor portion 31 connected to the sealing membrane 2, a support portion 32 located outside the sealing membrane 2, and a protrusion portion 33 extending outwardly from the support portion 32 for frictional positioning with the adjacent tissue, wherein the material of the strand at the support portion 32 is modified to obtain a higher rigidity for further supporting the protrusion portion 33.

Figure 31:
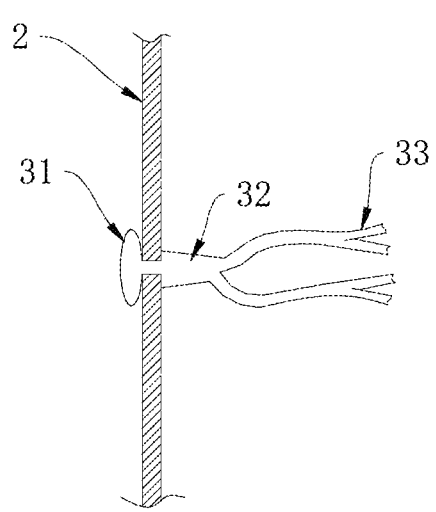
FIG. 31 is a schematic structural view of a support portion of an interventional instrument according to an embodiment.

Referring to FIG. 31, in another embodiment, the interventional instrument includes a stent, a sealing membrane 2 covering the stent, and a friction increasing member distributed on the sealing membrane 2. The friction increasing member is configured as a strand, including an anchor portion 31 connected to the sealing membrane 2, a support portion 32 located outside the sealing membrane 2, and a protrusion portion 33 extending outwardly from the support portion 32 for frictional positioning with the adjacent tissue, wherein the strand is thickened at the support portion 32 to obtain a higher rigidity for further supporting the protrusion portion 33.

Figure 32:
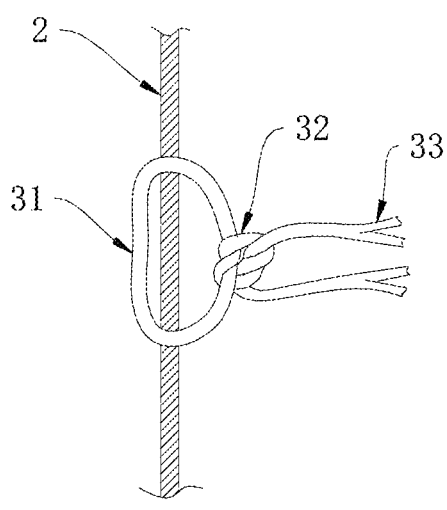
FIG. 32 is a schematic structural view of a support portion of an interventional instrument according to an embodiment.

Referring to FIG. 32 and the above-mentioned related figures, in another embodiment, the interventional instrument includes a stent, a sealing membrane 2 covering the stent, and a friction increasing member distributed on the sealing membrane 2. The friction increasing member is configured as a strand, including an anchor portion 31 connected to the sealing membrane 2, a support portion 32 located outside the sealing membrane 2, and a protrusion portion 33 extending outwardly from the support portion 32 for frictional positioning with the adjacent tissue, wherein the strand at the support portion 32 is knotted to obtain a higher rigidity for further supporting the protrusion portion 33. In the present embodiment, the friction increasing member is formed by one single strand, two arms extending from the U-shaped anchor portion 31 are knotted with each other to form the support portion 32, and the protrusion portion is formed as a branched structure by disassembling and splitting the strand. The strand sections for the protrusion portion point to the same or different directions.

Figure 33:
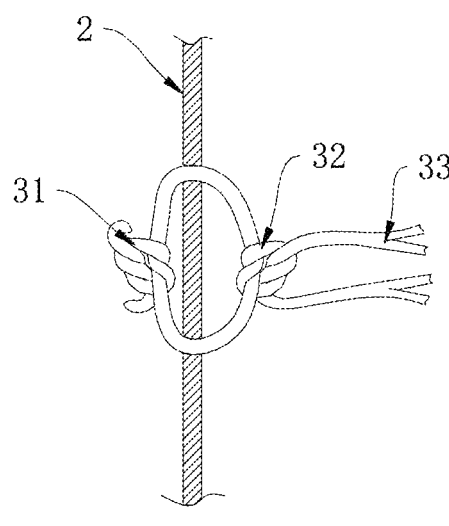
FIG. 33 is a schematic structural view of a support portion of an interventional instrument according to an embodiment.

In another embodiment, for example, as shown in FIG. 33, the friction increasing member is formed by two strands, wherein both the anchor portion 31 and the support portion 32 are formed by knotting the two strands, and the protrusion portion is formed as a branched structure by disassembling and splitting the strand.

Figure 34:
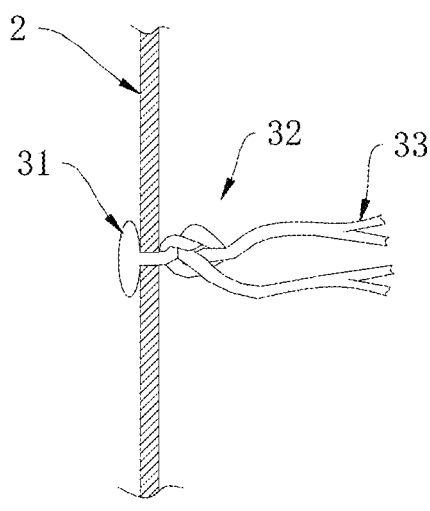
FIG. 34 is a schematic structural view of a support portion of an interventional instrument according to an embodiment.

In another embodiment, for example, as shown in FIG. 34, the friction increasing member is formed by one single strand, wherein the support portion 32 is formed by knotting the strand, and the protrusion portion is formed as a branched structure by disassembling and splitting the strand.

Referring to FIG. 35, the support portion can be configured as a separate member that is separated from both the anchor portion and the protrusion portion. In the present embodiment, the interventional instrument includes a stent, a sealing membrane 2 covering the stent, and a friction increasing member distributed on the sealing membrane 2. The friction increasing member is configured as a strand, including an anchor portion 31 connected to the sealing membrane 2, a support portion 32 located outside the sealing membrane 2, and a protrusion portion 33 extending outwardly from the support portion 32 for frictional positioning with the adjacent tissue, wherein the support portion 32 is configured as a gasket and has a higher rigidity than the protrusion portion 33 and the anchor portion 31, and wherein the anchor portion 31 passes through the gasket on the sealing membrane 2 and further extends to form the protrusion portion 33. In another embodiment, the support portion 32 can be configured as a sleeve, the anchor portion 31 passes through the sleeve on the sealing membrane 2 and further extends to form the protrusion portion 33, wherein the support portion 32 is sandwiched and limited between the sealing membrane 2 and the protrusion portion 33.

In order to prevent the friction increasing members in different hollowed-out areas from being dragged with each other to affect the loading when the state of the stent is changed, in a preferred embodiment, the support portions of the friction increasing members in different hollowed-out areas are provided independently from each other. The support portions of all the friction increasing members in the same hollowed-out area can be formed in one piece, or the support portions of the friction increasing members in the same hollowed-out area can be provided independently from each other.

As the support portions in different hollowed-out areas are respectively provided independently, the outer wall of the frame bars of the stent can be prevented from being surrounded by the support portions. If the support portions surround the periphery of the stent, the support portions with high rigidity will be inevitably adverse to the loading process. In a further preferred embodiment, in the loaded state of the stent, the driving portions are folded, and the support portions are surrounded by the respective folded driving portions and are located in the receiving space (see FIG. 3 which shows the detail). In a further preferred embodiment, in the loaded state, the protrusion portions are surrounded by the folded driving portions and are located in the receiving space.

In the above embodiments, in the case where the friction increasing member uses strand, the end of the strand section for the protrusion portion away from the support portion is a free end, and the free end is further expanded than the rest of the strand section for the protrusion portion. As shown in FIG. 36, the protrusion portion 33 is expanded by untwisting, that is, forming an untwisted region 332; alternatively, the protrusion portion 33 can be expanded by local hot-melt and deformation, that is, forming a hot-melt region 333.

Referring to FIGS. 37 and 38, in another embodiment, an inner sealing membrane is sewn to the inside of the stent of the interventional instrument. In a hollowed-out area of the stent, the friction increasing member 3 is provided on the driving portion 23 of the inner sealing membrane in the form of a strand. The driving portion 23 is provided with a plurality of connection holes, and the strand is sewn to pass through the inside and the outside of the driving portion 23 back and forth via the connection holes to form the anchor portion 31 and the protrusion portion 33, and the support portion 32 is formed by knotting the strand for the protrusion portion 33 near the outside of the driving portion 23. In the present embodiment and in the same driving portion 23, the friction increasing member 3 includes a plurality of units. As shown in the figure, the friction increasing member 3 includes three strands, which are respectively wound and knotted. The structure for the respective units can independently use any of the structures described above in connection with FIGS. 30 to 36.

In order to avoid axial pulling of the friction increasing member when the inner sealing membrane 2 is circumferentially folded, the units and thus the connection holes are provided in sequence along the axial direction of the stent.

Figures 39, 40:
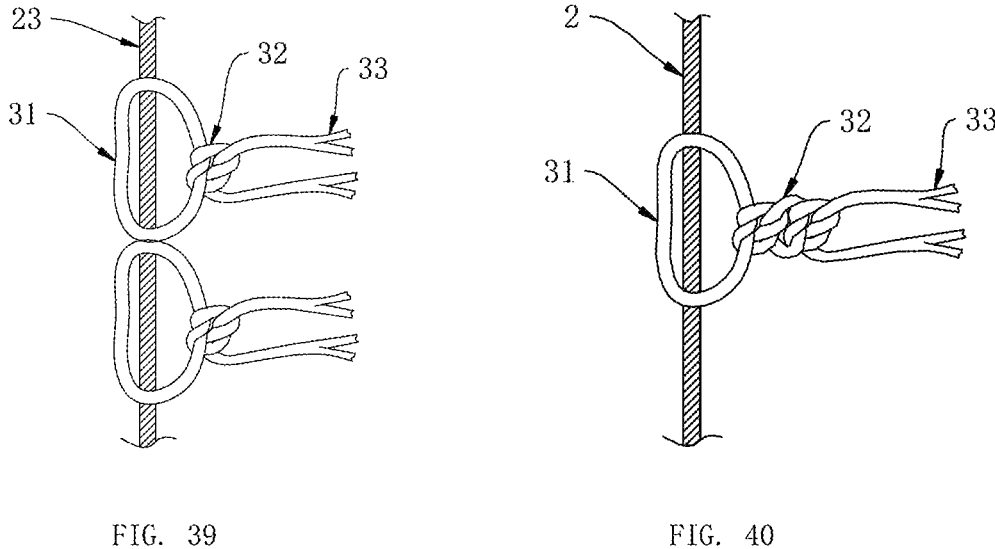
FIG. 39 is a schematic structural view of a friction increasing member of an interventional instrument according to an embodiment
FIG. 40 is a schematic structural view of a friction increasing member of an interventional instrument according to an embodiment.

Furthermore, the number of the strands and thus the number of the units of the friction increasing member 3 can be increased or decreased as required. Referring to FIG. 39, in another embodiment, the friction increasing member 3 includes two units, and as shown in the figure, the friction increasing member includes two strands which are respectively wound and knotted. The structure for the respective units can independently use any of the structures described above in connection with FIGS. 30 to 36.

In order to ensure the rigidity of the support portion and to prevent the portion of the friction increasing member outside the stent from falling down after the stent is released, the strand for the friction increasing member can be knotted multiple times in succession to form the support portion.

Figures 41, 42:
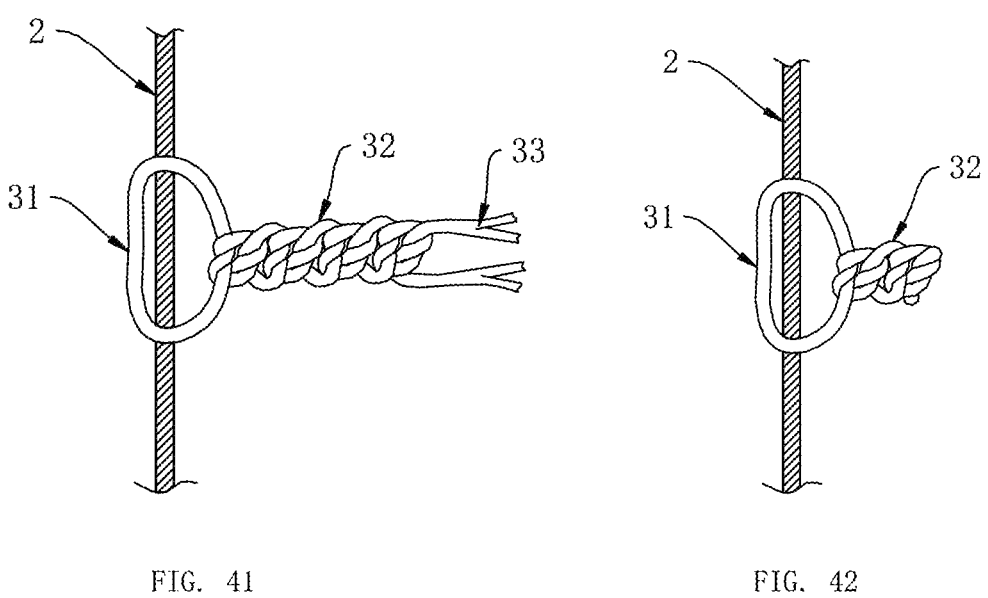
FIG. 41 is a schematic structural view of a friction increasing member of an interventional instrument according to an embodiment.
FIG. 42 is a schematic structural view of a friction increasing member of an interventional instrument according to an embodiment.
Figures 43, 44, 45, 46:
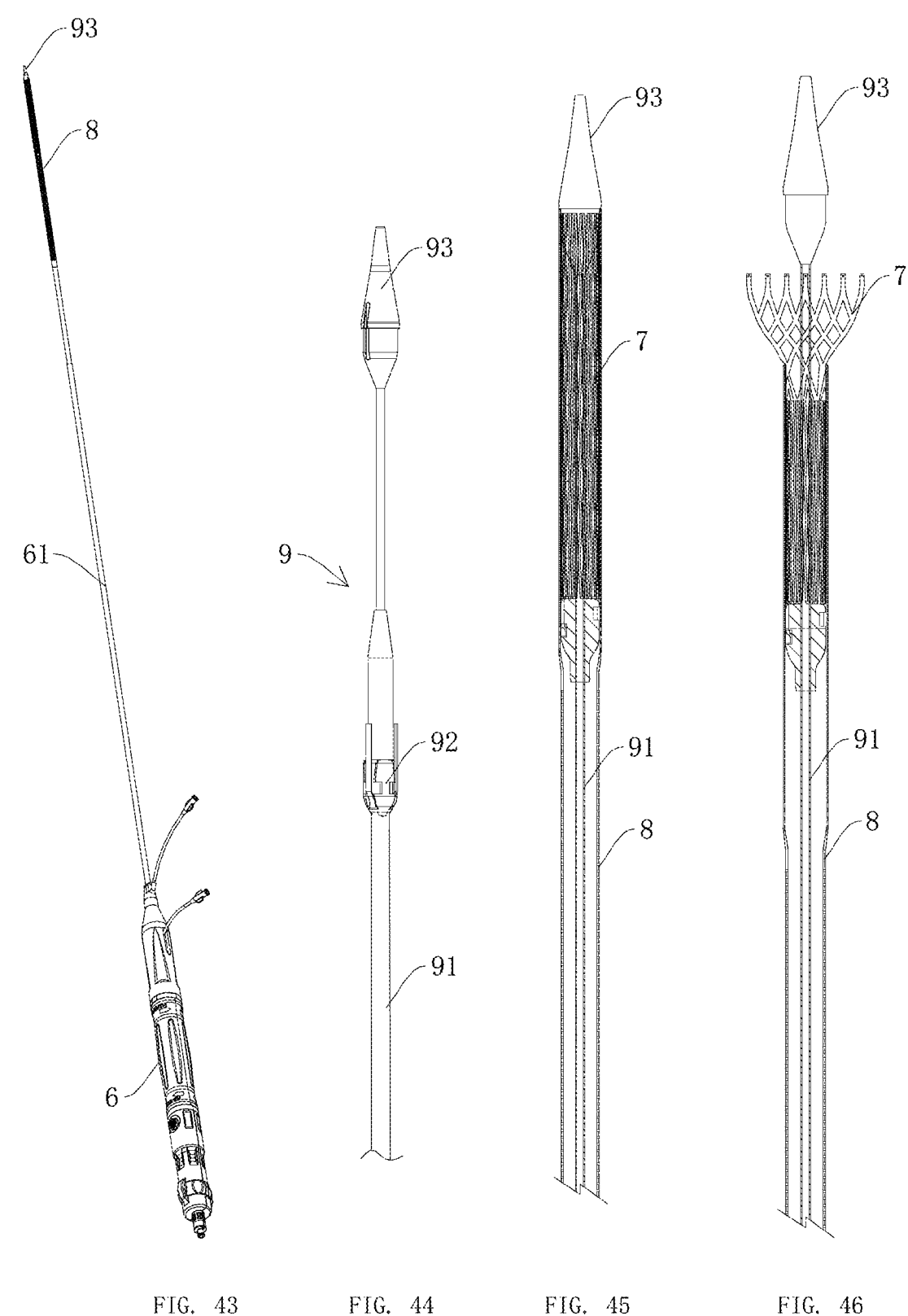
FIG. 43 is a schematic structural view of an intervention system according to an embodiment of the present application.
FIG. 44 is a schematic structural view of a core assembly shown in FIG. 43.
FIG. 45 is a schematic view of an interventional instrument in a compressed state before release.
FIG. 46 is a schematic view of an interventional instrument with the distal end thereof partially expanded during release.

Referring to FIG. 40, in one embodiment, the inside of the stent of the interventional instrument is sewn with a sealing membrane 2, i.e. the sealing membrane 2 is configured as an inner sealing membrane. In a hollowed-out area of the stent, the friction increasing member is provided on the driving portion of the inner sealing membrane in the form of strand, including an anchor portion 31 connected to the sealing membrane 2, a support portion 32 located outside the sealing membrane 2, and a protrusion portion 33 extending outwardly from the support portion 32 for frictional positioning with the adjacent tissue. In the present embodiment, the friction increasing member is formed by one strand, with the U-shaped anchor portion 31 passing through the sealing membrane 2 via the connection holes of the sealing membrane 2, the two arms thereof knotted with each other to form the support portion 32, and the strand section of the knotted strand further extending to form the protrusion portion 33 the end of which forms a branched structure by disassembling and splitting. The support portion 32 can be knotted multiple times in succession. As shown in the figure, the support portion 32 is knotted four times. In other embodiments, the support portion 32 can have more or fewer knots, for example, in another embodiment as shown in FIG. 41, the support portion 32 is knotted eight times.

In contrast to the embodiment of FIG. 40, it is possible to omit the protrusion portion. For example, in another embodiment as shown in FIG. 42, the inside of the stent of the interventional instrument is sewn with a sealing membrane 2, i.e. the sealing membrane 2 is configured as an inner sealing membrane. In a hollowed-out area of the stent, the friction increasing member is provided on the driving portion of the inner sealing membrane in the form of strand, including an anchor portion 31 connected to the sealing membrane 2 and a support portion 32 located outside the sealing membrane 2, with the U-shaped anchor portion 31 passing through the sealing membrane 2 via the connection holes of the sealing membrane 2 and the two arms thereof knotted with each other multiple times to form the support portion 32, without further outward extension of the knotted strand, i.e., without a protrusion portion having an obvious change in rigidity.

In one embodiment according to the present application, a method for processing an interventional instrument is provided for using the interventional instrument described in the above embodiments independently or in combination. For example, the interventional instrument includes a stent, which has a frame structure with hollowed-out area(s) and has an axis. The stent has a radially compressed loaded state and a radially expanded released state. The processing method includes the following steps in any order:

In step S100, a sealing membrane(s) is mounted on the stent. The sealing membrane(s) is connected with the stent and corresponds to at least a part of the hollowed-out area(s).

In the loaded state, the outer peripheral surface of the stent encloses a receiving space, and the sealing membrane(s) is located in the receiving space. The sealing membrane(s) is deformed by pulling of the stent when the state of the stent is changed.

In step S200, a friction increasing member(s) is mounted on the sealing membrane(s). In the released state, the friction increasing member(s) extends to the outside of the stent for friction positioning with the adjacent tissue at the implantation site for the interventional instrument.

In a preferred embodiment, in step S100, the sealing membrane(s) is configured as an inner sealing membrane for contacting the inside of the stent, and the inner sealing membrane covers the inside of the stent and is fixed by sewing during mounting.

In a preferred embodiment, in step S200, the friction increasing member is configured as a strand(s). During mounting, one end of the strand is inserted through the inner sealing membrane from the outside of the stent into the inside of the stent, then passes through the inner sealing membrane from the other position of the same hollowed-out area back to the outside of the stent, and is knotted with the other portion of the strand outside the stent, with at least one strand section of the knotted strand further extending towards the outside of the stent for friction positioning with the adjacent tissue.

FIGS. 43-46 show an interventional system according to one embodiment of the present application. The interventional system includes a sheath assembly, a control handle 6 and an interventional instrument 7. The sheath assembly has opposite distal and proximal ends. The interventional instrument 7 is loaded in the distal end of the sheath assembly. The control handle 6 is connected to the proximal end of the sheath assembly. The interventional instrument 7 can be released by driving the sheath assembly through the control handle. The interventional instrument 7 can be the interventional instrument according to the embodiments described above.

The sheath assembly includes a sheath 8 and a core assembly 9. The sheath 8 is slidably engaged with the outer periphery of the core assembly 9. The core assembly 9 includes a core tube 91, and a locking member 92 fixed to the core tube for connecting the interventional instrument 7. The distal end of the core tube 91 further extends out of the locking member 92 and is fixed with a guide head 93. The distal end of the guide head 93 has a tapered and rounded head structure for facilitating travel in the human body. The space between the guide head 93 and the locking member 92 can be used as a loading position for the interventional instrument 7. The interventional instrument 7 in the compressed state is located at this position and is in positive engagement with the locking member 92.

In other embodiments, the interventional system can further include a catheter 61 fixed with the control handle 6 for providing a channel to prevent injury to the tissue in vivo when the sheath 8 moves back and forth.

The interventional instrument 7 is loaded on the core assembly 9 and surrounded by the sheath 8 and enters the body along with the catheter 61, and the sheath 8 is then slidably retracted proximally relative to the core assembly 9 by the control handle 6, thereby gradually exposing and releasing the interventional instrument 7.

The features described in the above various embodiments can be combined. In order to simplify the descriptions, not all possible combinations of the features in the above embodiments have been described. However, any combinations of the features should be within the scope of the invention as long as no conflict resides among these features. In the case where the features in different embodiments are shown in the same drawing, it may be considered that this drawing discloses a combination of the various embodiments involved.

The above embodiments are only several implementations of the present invention which are described specifically and in detail, without limitation to the scope claimed by the present invention. Those skilled in the art can make various modifications and variations to the embodiments without departing from the spirit and scope of the present invention, and these modifications and variations should fall into the scope claimed by the present invention. Therefore, the scope of protection of the invention patent should be subject to the attached claims.

What is claimed is:

1. An interventional instrument facilitating positioning, comprising:

a stent, which has a frame structure with at least one hollowed-out area and has an axis, the stent having a loaded state in which the stent is radially compressed and a released state in which the stent is radially expanded;

a sealing membrane, which is connected to the stent and seals at least part of the at least one hollowed-out area, wherein in the loaded state, the stent encloses a receiving space, and the sealing membrane is located in the receiving space, and wherein the sealing membrane is an inner sealing membrane that contacts an inside of the stent; and at least one friction increasing member which is connected to the sealing membrane and separated from the stent, wherein the at least one friction increasing member is one or more strands configured with elasticity;

wherein the frame structure is configured as a meshed structure, each of the at least one hollowed-out area is configured as a mesh hole, and each of the at least one friction increasing member comprises:

an anchor portion connected to a portion of the sealing membrane sealing one of the mesh holes;

a support portion outside the sealing membrane in a radial direction of the stent; and a protrusion portion extending from the support portion towards an outside of the stent for frictional positioning with an adjacent tissue;

wherein the anchor portion, the support portion and the protrusion portion separately use one or more strands, or at least two of the anchor portion, the support portion and the protrusion portion share one strand; and wherein the anchor portion passes through the sealing membrane via at least one connection hole, and a part of the anchor portion located inside the sealing membrane is provided with an anchor head which is blocked by the at least one connection hole.

2. The interventional instrument facilitating positioning of claim 1, wherein the stent has an axial passage therein, and wherein in the released state, the axial passage is opened, or at least one leaflet is arranged in the stent for closing or opening the axial passage.

3. The interventional instrument facilitating positioning of claim 1, wherein the stent is provided with an auxiliary positioning structure for interacting with an adjacent tissue, and the auxiliary positioning structure is configured as a slip resistant texture on an outer surface of the stent.

4. The interventional instrument facilitating positioning of claim 1, wherein the stent is configured to be circumferentially expanded during release, and the sealing membrane is configured to act with the circumferential expansion of the stent to drive the at least one friction increasing member to change a radial position of the at least one friction increasing member; and wherein in the loaded state, the at least one friction increasing member is entirely located in the receiving space of the stent; and in the released state, the at least one friction increasing member extends partly to an outside of the stent radially.

5. The interventional instrument facilitating positioning of claim 1, wherein at least a portion of the sealing membrane is configured as a driving portion corresponding to the respective hollowed-out area; and the driving portion is configured to be folded in the loaded state, with at least a portion of the respective friction increasing member surrounded by the folded driving portion.

6. The interventional instrument facilitating positioning of claim 5, wherein an edge of the driving portion contacts a radial inside of the stent.

7. The interventional instrument facilitating positioning of claim 1, wherein the at least one friction increasing member comprises a plurality of friction increasing members; and in the released state, the friction increasing members are distributed in a circumferential direction of the stent, and each of the friction increasing members corresponds to the respective mesh hole in position.

8. The interventional instrument facilitating positioning of claim 7 wherein the plurality of friction increasing members are divided into a plurality of groups, each group comprises at least two of the friction increasing members that are arranged in a row along the circumferential direction of the stent, and adjacent groups are offset from each other in an axial direction and the circumferential direction of the stent.

9. The interventional instrument facilitating positioning of claim 7, wherein one or more friction increasing members are disposed within one of the hollowed-out areas.

10. The interventional instrument facilitating positioning of claim 1, wherein the anchor portion vertically passes through the sealing membrane.

11. The interventional instrument facilitating positioning of claim 1, wherein the support portion has a higher rigidity than the protrusion portion.

12. The interventional instrument facilitating positioning of claim 11, wherein the protrusion portion comprises one or more strand sections, and at least one of the strand sections is enlarged in diameter at an end thereof close to the sealing membrane to form the support portion, or at least one of the strand sections has a higher rigidity at an end thereof close to the sealing membrane than at the other end thereof away from the sealing membrane.

13. The interventional instrument facilitating positioning of claim 1, wherein the support portion is a gasket or a sleeve, and the protrusion portion extends through the support portion or abuts against the support portion.

14. The interventional instrument facilitating positioning of claim 1, wherein the protrusion portion is one or more branched strand sections of the strand.

15. The interventional instrument facilitating positioning of claim 14, wherein one end of the strand section away from the support portion is a free end which is further expanded than the rest of the strand section by untwisting or local hot melt deformation.

16. An interventional instrument facilitating positioning, comprising:

a stent, which has a frame structure with at least one hollowed-out area and has an axis, the stent having a loaded state in which the stent is radially compressed and a released state in which the stent is radially expanded;

a sealing membrane, which is connected to the stent and seals at least part of the at least one hollowed-out area, wherein in the loaded state, the stent encloses a receiving space, and the sealing membrane is located in the receiving space, and wherein the sealing membrane is an inner sealing membrane that contacts an inside of the stent; and at least one friction increasing member which is connected to the sealing membrane and separated from the stent, wherein the at least one friction increasing member is one or more strands configured with elasticity;

wherein the frame structure is configured as a meshed structure, each of the at least one hollowed-out area is configured as a mesh hole, and each of the at least one friction increasing member comprises:

an anchor portion connected to a portion of the sealing membrane sealing one of the mesh holes;

a support portion outside the sealing membrane in a radial direction of the stent; and a protrusion portion extending from the support portion towards an outside of the stent for frictional positioning with an adjacent tissue;

wherein the anchor portion, the support portion and the protrusion portion separately use one or more strands, or at least two of the anchor portion, the support portion and the protrusion portion share one strand; and wherein the anchor portion vertically passes through the sealing membrane.

* * * * *